United States Patent [19]

Forester

[11] Patent Number: 4,962,264
[45] Date of Patent: Oct. 9, 1990

[54] METHODS FOR RETARDING COKE FORMATION DURING PYROLYTIC HYDROCARBON PROCESSING

[75] Inventor: David R. Forester, Conroe, Tex.
[73] Assignee: Betz Laboratories, Inc., Trevose, Pa.
[21] Appl. No.: 425,622
[22] Filed: Oct. 23, 1989
[51] Int. Cl.$^5$ .................................................. C07C 4/02
[52] U.S. Cl. .............................. 585/648; 208/48 AA; 208/48 R; 585/651; 585/950
[58] Field of Search ................ 208/48 AA; 585/648, 585/651, 950

[56] References Cited

U.S. PATENT DOCUMENTS

| | | | |
|---|---|---|---|
| 1,900,739 | 3/1933 | Schmidt et al. | 585/648 |
| 3,531,394 | 9/1970 | Koszman | 208/48 |
| 3,583,903 | 6/1971 | Miale et al. | 585/648 |
| 3,903,186 | 9/1975 | Ohsumi et al. | 208/48 AA |
| 4,105,540 | 8/1978 | Weinland | 208/48 |
| 4,188,281 | 2/1980 | Wernicke et al. | 585/648 |
| 4,297,246 | 10/1981 | Cairns et al. | 252/465 |
| 4,680,421 | 7/1987 | Forester et al. | 585/648 |
| 4,747,931 | 5/1988 | Forester et al. | 208/14 |
| 4,756,820 | 7/1988 | Reid et al. | 208/48 |

*Primary Examiner*—Helane Myers
*Attorney, Agent, or Firm*—Alexander D. Ricci; Bruce E. Peacock

[57] ABSTRACT

Methods are disclosed for inhibiting coke formation in pyrolytic reactors or furnaces during the pyrolysis operation. Rare earth elements or compounds thereof, such as cerium and lanthanum elements or compounds, are added to the particular hydrocarbonaceous medium undergoing such pyrolysis.

21 Claims, No Drawings

METHODS FOR RETARDING COKE FORMATION DURING PYROLYTIC HYDROCARBON PROCESSING

FIELD OF THE INVENTION

The present invention pertains to methods for inhibiting the formation and deposition of coke deposits during the high temperature processing or cracking of hydrocarbons by the use of rare earth elements or compounds either dissolved or dispersed in a liquid carrier.

BACKGROUND OF THE INVENTION

Coke deposition is generally experienced when hydrocarbon liquids and vapors contact the hot metal surfaces of processing equipment. While perhaps not entirely technically understood, because of the complex makeup of the hydrocarbons, the hydrocarbons at elevated temperatures and in contact with hot metallic surfaces undergo various changes through either chemical reactions and/or decomposition of various unstable components of the hydrocarbon. The undesired products in many instances include coke, polymerized products, deposited impurities and the like. Whatever the undesired product that may be formed, the result is the same, i.e., reduced economies of the process. If these deposits are allowed to remain unchecked, heat transfer, throughput and overall productivity are detrimentally effected. Moreover, downtime is likely to be encountered due to the necessity of either replacing and/or cleaning of the affected parts of the processing system.

While the formation and type of undesired products are dependent upon the hydrocarbon being processed and the conditions of the processing, it may generally be stated that such products can be produced at temperatures as low as 100° F.; but are much more prone to formation as the temperature of the processing system and the metal surfaces thereof in contact with the hydrocarbon increase. At these temperatures, coke formation is likely to be produced regardless of the type hydrocarbon being charged. The type coke formed, i.e., amorphous, filamentous or pyrolytic, may vary somewhat; however, the probability of the formation of such is quite high.

As indicated in U.S. Pat. Nos. 3,531,394 and 4,105,540 the teachings of which are incorporated herein by reference, coke formation and deposition are common problems in ethylene (olefin) plants which operate at temperatures where the metal surfaces in contact with the hydrocarbon are sometimes at 1600° F. and above. The problem is prevalent in the cracking furnace coils as well as in the transfer line exchanger where pyrolytic type coke formation and deposition is commonly encountered. Ethylene plants, often referred to generally as "olefin plants", originally produced simple olefins such as ethylene, propylene, butanes and butadiene from a feed of ethane, propane, butanes and mixtures thereof. Later developments in the area of technology however, have led to the cracking of heavier feedstocks, because of their availability, to produce aromatics and pyrolysis gasoline as well as light olefins. Feedstocks now include light naphtha, heavy naphtha and gas oil. According to the thermal cracking processes utilized in olefin plants, the feedstocks are cracked generally in the presence of steam in tubular pyrolysis furnaces. The feedstock is preheated, diluted with steam and the mixture heated in the pyrolysis furnace to about 1500° F. and above, most often in the range of 1500° F. to 1650° F. The effluent from the furnace is rapidly quenched by direct means or an exchanger which is used to generate high pressure steam at 400 to 800 psig for process use. This rapid quench reduces the loss of olefins by minimizing secondary reactions. The cooled gas then passes to the prefractionator where it is cooled by circulating oil streams to remove the fuel oil fraction. In some designs, the gas leaving the quench exchanger is further cooled with oil before entering the prefractionator. In either case, the heat picked up by the circulating oil stream is used to generate steam and to heat other process streams. The mixture of gas and steam leaving the prefractionator is further cooled in order to condense the steam and most of the gasoline product in order to provide reflux for the prefractionator. Either a direct water quench or heat exchanger is used for this cooling duty.

After cooling, cracked gas at, or close to atmospheric pressure, is compressed in a multistage compression system to much higher pressures. There are usually four or five stages of compression with interstage cooling and condensate separation between stages. Most plants have hydrocarbon condensate stripping facilities. Condensate from the interstage knockout drums is fed to a stripper where the $C_2$ hydrocarbons and lighter, are separated. The heavier hydrocarbons are fed to the depropanizer.

PRIOR ART

A variety of approaches have been proposed to eliminate coke formation during the elevated temperature processing of hydrocarbonaceous mediums. For example, U.S. Pat. No. 4,680,421 (Forester et al.—of common assignment herewith) teaches utilization of ammonium borates, specifically ammonium biborate and ammonium pentaborate that are preferably dissolved in a glycollic solvent. See also U.S. Pat. No. 4,747,931 (Forester et al.). Of similar import is U.S. Pat. No. 4,756,820 (Forester et al.—also of common assignment herewith) which discloses that boron oxides, borates, borate esters, peroxyborates, boranes, organoboranes, borazine and salts of boron may be used.

U.S. Pat. No. 4,297,246 (Cairns et al.) teaches that coatings obtainable from sols, such as $CeO_2$, $SiO_2$, $ZrO_2$, and $TiO_2$, may be used to protect substrates. The desired substrate is first immersed in the sol, followed by removal and drying to convert the sol to the corresponding gel. Typical environments for such protection include use on metallic substrates to protect the metals from oxidative attack and for inhibiting deposition of carbon layers on steel surfaces exposed to hydrocarbon-containing environments. (See, for instance, column 4, lines 62 et seq). In order for the oxide sols to be effective, they must be used to pretreat the metal surfaces at low temperatures, then heat treated in air (850°–1000° C.) to convert the sol to an oxide coating on the requisite surface. The disclosure is devoid of suggesting that the sols could be used to treat the metal surfaces or the hydrocarbon stream while the process is in progress as is the case in the present invention wherein the disclosed coke retarding treatments are used and are effective during the high temperature pyrolytic cracking process.

Despite the prior art efforts, there remains a need for an inexpensive, but effective treatment for use to inhibit the formation and deposition for coke particles on heated surfaces in a high temperature (i.e., ≧1400° F.) pyrolysis furnace that is adapted to crack petroleum gases or liquids to make olefins such as in the high temperature cracking of propane to make ethylene/propylene.

DESCRIPTION OF THE INVENTION

Generally, the invention entails utilizing rare earth elements or compounds thereof to inhibit coke formation in pyrolytic processing applications. As used herein, the designation "rare earth" is defined as including fifteen elements in Group IIIB of the periodic chart specified as follows:

|  |  | Atomic Number |
|---|---|---|
| lanthanum | La | 57 |
| cerium | Ce | 58 |
| praeseodymium | Pr | 59 |
| neodymium | Nd | 60 |
| promethium | Pm | 61 |
| samarium | Sm | 62 |
| europium | Eu | 63 |
| gadolinium | Gd | 64 |
| terbium | Tb | 65 |
| dysprosium | Dy | 66 |
| holmium | Ho | 67 |
| erbium | Er | 68 |
| thulium | Tm | 69 |
| ytterbium | Yb | 70 |
| lutetium | Lu | 71 |

The elements 57–62 are sometimes referred to as the cerium subgroup with the remainder being known as the yttrium subgroup.

Any suitable form of the rare earths may be utilized to inhibit coke formation in accordance with the invention. Elemental rare earths, inorganic rare earth compounds and organic rare earth compounds as well as mixtures of any two or more thereof are suitable rare earth sources.

Examples of such inorganic rare earth compounds include the oxides, salts such as the nitrates, ammonium nitrates, carbonates, phosphates, sulfates, and halides, including the chlorides, fluorides, bromides and iodides (not preferred due to formation of corrosive by-products), hydroxides and any hydrated salts of the above.

Organic rare earth containing compounds include the salts of organic acids such as oxalic acid, the acetate salts, octoates, ethylhexanoates, napthenates, acetyl acetonates, citrates, salicylates, etc.

Due to the cost considerations, elemental cerium and lanthanum and their compounds are preferred. Exemplary cerium and lanthanum compounds include:
cerous ammonium nitrate
cerous ammonium sulfate
cerium octoate
cerium (IV) oxide
ceric fluoride
ceric sulfate
cerous bromide
cerous carbonate
cerous chloride
cerous fluoride
cerous iodide
cerous nitrate hexahydrate
cerous oxalate
cerous sulfate
cerous acetate
lanthanum nitrate hexahydrate
lanthanum chloride
lanthanum oxide
lanthanum acetate
lanthanum octoate, and
lanthanum sulfate The methods of the invention are adapted to inhibit the formation and deposition of coke on metallic surfaces in contact with a hydrocarbon (either in liquid or gaseous form) which surfaces reach temperatures of 1400° F. and above (most often 1500°–2050° F.) These temperatures are commonly encountered in olefin plants as earlier indicated. In these systems, the components of the furnace (pyrolytic) as well as the ancillary parts are composed of ferrous metal. Iron, as well as iron alloys such as low and high carbon steel, and nickel-chromium-iron alloys are customarily used for the production of hydrocarbon processing equipment such as furnaces, transmission lines, reactors, heat exchangers, separation columns, fractionators, and the like.

It has been found that coking during the high temperature cracking of hydrocarbons may be significantly reduced on heated stainless steel surfaces utilized in conjunction with the test system described infra by use of the rare earth elements and/or compound treatments noted in the examples. Accordingly, it is to be expected that coking will also be reduced on iron, chromium and nickel based metallurgical surfaces in contact with pyrolysis products in high temperature pyrolytic furnaces.

The rare earth elements or compounds may be added directly to the hydrocarbon feedstock or charge before and/or during cracking, or the treatment may be mixed with steam carried to the cracking zone in accordance with conventional cracking techniques.

The rare earths may be dissolved or dispersed in a suitable carrier liquid. Depending upon the particular compound utilized either polar or non-polar carrier liquids may be used. Preferred polar carrier liquids comprise water, alcohols (methanol, ethanol, etc.) and glycols. Examples of non-polar carrier liquids include paraffinic or aromatic hydrocarbons such as light oil, heavy aromatic naphtha, and kerosene and the like.

Generally, the rare earth compound is dissolved or dispersed in a polar carrier liquid in a concentration that will produce the necessary amount of rare earth to the coke-prone environment to inhibit or reduce coking. Coking is a significant problem and if left untreated will eventually shut the operation down. Accordingly, it is desirable to ensure that the rare earth source content of the carrier solution or dispersion is high enough to ensure that an ample quantity of the rare earth mixes with or is dispersed in the hydrocarbonaceous medium during the pyrolytic cracking process. Accordingly, product formulation lends itself to great flexibility.

The coke retarding product can contain, on a weight basis, from about 1–75% active materials (rare earth element or compound thereof) either dissolved or dispersed in a carrier liquid, preferably polar solvent. To assure maintenance of the solution or dispersion during storage and transport, stabilizing agents and/or preservatives may also be added to the formulation.

EXAMPLES

In order to establish the efficacy of the invention, various tests were conducted using a propane feedstock with dilution steam added to enhance cracking. The apparatus and procedure used for the testing were as follows:

Apparatus

The High Temperature Fouling Apparatus (HTFA) consists of five subsections which together simulate the pyrolysis of gaseous hydrocarbons to make the light olefinic end products and the undesirable by-product, coke, that is formed on the heated metal surfaces during the pyrolysis reaction.

The feed preheat section is built of 316 stainless steel tubing and fittings and allows the mixing of nitrogen or oxygen containing gas with steam during the start up and shut down of the HTFA and the propane with steam during the actual test. Steam is supplied at 40 psig by a steam generator and nitrogen, oxygen containing gas, or propane is fed from compressed gas cylinders. The gases and steam are heated to about 300° F. at which point small amounts of water (blank test) or candidate material is slowly injected into the stream by a syringe pump. The gases/candidate material are further preheated to about 500° F. before flowing through a 13-foot long coiled 316 SS tube inside an electrically heated furnace. The gases are heated at a furnace temperature of approximately 1880 F. and exit the furnace at 1150°-1450° F.

Following the furnace tube, the gases travel through the coker rod assembly. This consists of a 316 SS rod which is electrically heated to 1500° F. while the gases flow around the heated rod inside a 316 SS shell. The rod is electrically heated through a silicon controlled rectifier (SCR), then through two 4 to 1 stepdown transformers in series to achieve low voltage (3–4 volts), high amperage (200 amps) heating of the rod. A temperature controller is used to achieve power control through the SCR to obtain a 1500° F. rod temperature.

Upon exiting the coker rod, the gases pass through a condenser coil and then through three knock-out flasks in ice baths to remove the water (steam) from the product gases. The small amount of remaining entrained water vapor in the gases is removed by passing through drierite granules.

The specific gravity of the product gas is determined in a gas densitometer and the gases are analyzed using gas chromatography to determine yields. The remaining gases are vented through a safety hood exhaust.

Test Procedure

The furnace was turned on and the temperature thereof was stabilized at 1300° F. while feeding nitrogen and steam. The coker rod was heated to 1500° F. The nitrogen was replaced with oxygen containing gas (air) and furnace temperatures were then slowly increased to 1500° F. over a period of ten minutes. Then the air was replaced with nitrogen and the coke inhibitor or water (blank), as the case may be, was injected into the mixed gas or steam line at about 300° F. gas temperature while the furnace temperature was slowly raised to 1880° F. over 20–25 minutes.

Then the nitrogen feed was gradually switched to propane feed over about 5 minutes. The temperature of the furnace dropped due to the propane cracking reaction and was allowed to increase to the maximum attainable furnace temperature (1880° F. or less) over approximately a 30-minute period. The product gases were analyzed by gas chromatography and the temperatures, flowrates, pressures and product gas gravity recorded every 35 minutes during the 160-minute test on propane/steam feed. Gases exit the furnace tube at about 1150° F.–1450° F. and exit the coker shell at about 975°–1000° F. temperatures.

During a normal 160 minute run, approximately 3200–3300 grams of propane were fed and 1000–2000 grams of steam fed (determined from the condensate collected) for hydrocarbon to steam rates of about 1.6:1 to 3.2:1.

Following shutdown and cooling, the furnace tube and coker shell were cleaned and the coke collected and weighed. The coke was burned to determine how much was non-coke (metal corrosion products). These corrosion products (gray matter) were analyzed to be 69 wt. % $Fe_3O_4$, 13 wt. % $NiO$, 15 wt. % $Cr_2O_3$, 1 wt. % $SiO_2$, 1 wt. % $MnO_2$ and 1 wt. % loss on ignition. The composition is similar to 316 SS (68.4% Fe, 18% Cr, 11% Ni, 2.5% Mo and 0.1% carbon). After a series of blank (water) and candidate material tests were conducted, a steam to coke relationship was determined for the blanks and the predicted coke values compared to observed coke values of the treatments to determine percent coke reduction.

A summary of the 14 HTFA runs treated with cerium compounds and the four runs treated with lanthanum nitrate is shown in Table I.

TABLE I

High Temperature Fouling Apparatus Results
1300–1500° F. Furnace Steam/Air Decoking; 1500–1880° F. Furnace AF/N2/Steam;
1880° F. Furnace Propane (0.5 SCFM)/Steam/AF for 2.67 Hr.

| FT No./ Run No. | STEAM ml/min | ANTIFOULANT (metal, ppm) | COKE GMS | GRAY GMS | PREDICTED COKE, GMS(1) | % COKE(2) REDUCTION |
|---|---|---|---|---|---|---|
| 28-23 | 6.48 | 10% Ce(NO3)3*6H2O/H2O(51) | 0.35 | 0.09 | 0.82 | 57 |
| 21-9 | 8.04 | 10% Ce(NO3)3*6H2O/H2O(46) | 0.44 | 0.06 | 0.66 | 34 |
| 22-12 | 8.30 | 10% Ce(NO3)3*6H2O/H2O(46) | 0.28 | 0.21 | 0.64 | 56 |
| 24-4 | 10.05 | 10% Ce(NO3)3*6H2O/H2O(41) | 0.56 | 0.06 | 0.46 | −21 |
| 24-18 | 11.28 | 10% Ce(NO3)3*6H2O/H2O(33) | 0.27 | 0.18 | 0.41 | 35 |
| 30-11 | 7.59 | 17.5% Ce(NO3)3*6H2O/EG(95) | 0.87 | 0.74 | 0.61 | −42 |
| 25-8 | 11.54 | 2.5% CeO2susp/H2O(22) | 0.04 | 0.28 | 0.40 | 90 |
| 25-9 | 11.34 | 2.5% CeO2susp/H2O(22) | 0.04 | 0.37 | 0.41 | 90 |
| 25-17 | 9.48 | 2.5% CeO2susp/H2O(25) | 0.13 | 1.90 | 0.49 | 74 |
| 26-8 | 5.92 | 2.5% CeO2susp/H2O(26) | 0.40 | 0.53 | 0.79 | 49 |
| 26-11 | 6.54 | 2.5% CeO2susp/H2O(25) | 0.60 | 0.80 | 0.71 | 16 |
| 26-20 | 7.43 | 2.5% CeO2susp/H2O(25) | 0.34 | 2.22 | 0.63 | 46 |
| 30-10 | 7.29 | 4.5% CeO2susp/H2O(63) | 0.92 | 0.34 | 0.64 | −44 |
| 36-3 | 12.26 | 35% NH4CeNO3/EG(159) | 0.65 | 0.61 | 0.60 | −8 |
| 18-11 | 7.00 | 10% La(NO3)3*6H2O/H2O(46) | 0.55 | 0.06 | 0.76 | 28 |
| 19-7 | 5.47 | 10% La(NO3)3*6H2O/H2O(49) | 0.51 | 0.17 | 0.97 | 48 |
| 19-21 | 6.98 | 10% La(NO3)3*6H2O/H2O(44) | 0.72 | 0.14 | 0.76 | 6 |

TABLE I-continued

High Temperature Fouling Apparatus Results
1300–1500° F. Furnace Steam/Air Decoking; 1500–1880° F. Furnace AF/N2/Steam;
1880° F. Furnace Propane (0.5 SCFM)/Steam/AF for 2.67 Hr.

| FT No./ Run No. | STEAM ml/min | ANTIFOULANT (metal, ppm) | COKE GMS | GRAY GMS | PREDICTED COKE, GMS(1) | % COKE(2) REDUCTION |
|---|---|---|---|---|---|---|
| 21-14 | 9.39 | 10% La(NO3)3*6H2O/H2O(42) | 0.28 | 0.06 | 0.57 | 51 |

(1)PREDICTED COKE = A/CONDENSATE RATE (ml/min) WHERE A = 5.32 FOR FT'S (furnace tubes) 18-22, 4.65 FOR FT'S 24 TO 30, AND 7.38 FOR FT 36.
(2)% COKE REDUCTION = [1-COKE/PREDICTED COKE] * 100
(3)EG = ETHYLENE GLYCOL Average coke reductios obtained for each tested compound are summarized in Table II.

TABLE II

SUMMARY OF COKE REDUCTION EFFECTS OF CERIUM AND LANTHANUM CONTAINING COMPOUNDS AS TESTED IN THE HIGH TEMPERATURE FOULING APPARATUS

| COMPOUND | # OF HTFA RUNS | METAL (PPM) RANGE | AVERAGE COKE RE- DUCTION % | MANN-WHITNEY[1] CONFIDENCE LEVEL |
|---|---|---|---|---|
| CEROUS NITRATE HEXAHYDRATE | 6 | 33–95 | 20 | 93.6 |
| CERIUM OXIDE SUSPENSION | 7 | 22–63 | 46 | 99.7 |
| CERIC AMMONIUM NITRATE | 1 | 159 | −8 | — |
| ALL CERIUM TREATED RUNS | 14 | 22–159 | 31 | 99.7 |
| LANTHANUM NITRATE HEXAHYDRATE | 4 | 42–49 | 33 | 97.8 |
| BLANK | 62 | — | 0 | — |

[1]CONFIDENCE LEVEL THAT THE POOLED COKE REDUCTION LEVELS OF TREATED RUNS ARE GREATER THAN THE POOLED COKE REDUCTION LEVELS OF THE UNTREATED RUNS.

The pooled coke reduction values of each set of treated experiments were compared to the pooled coke reduction values from 62 untreated runs using the Mann-Whitney statistical comparison test. As shown in Table II, the average coke reduction of the six cerium nitrate treated runs was 20% and this level of coke reduction was greater than the untreated runs at the 93.6% confidence level. Additional satisfactory cerium nitrate treated runs would be expected to increase its confidence level above 95%. Similarly, the seven HTFA runs treated with cerium oxide suspension showed an average coke reduction level of 46% and a 99.7% confidence level. One run treated with ceric ammonium nitrate failed to show coke reduction for reasons unknown. Combining the coke reduction values for all 14 cerium treated HTFA runs showed an average coke reduction of 31% and a confidence level of 99.7%. The four HTFA runs treated with lanthanum nitrate exhibited an average coke reduction of 33% and a confidence level of 97.8%.

Accordingly, from the above, it is clear that the rare earth treatments are effective as coke retarding treatments under the simulated pyrolysis conditions above noted. These treatments would be expected to perform well at commonly encountered pyrolytic temperatures such as from 1400°–2100° F. Desirably, the rare earth elements or compounds should be added to the pyrolytic steam and/or hydrocarbon feedstock so as to provide about 0.1–5000 ppm of the desired rare earth metal, per million parts of the hydrocarbon feedstock. Based upon experimental data presently available, a preferred feed range is from about 5–100 ppm rare earth metal per million parts feedstock. At present, it is preferred to use a suspension of cerium oxide particles in water as the coke reduction treatment.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

I claim:

1. A method of inhibiting the formation and deposition of pyrolytic coke on the heated metal surfaces of the structural and associated parts of a pyrolysis furnace which is being used to crack a petroleum feedstock to produce lower and/or olefinic hydrocarbon fractions, which method comprises adding to the feedstock a coke inhibiting amount of a rare earth element or rare earth containing compound.

2. A method as recited in claim 1 wherein said surfaces are heated, during said cracking, to a temperature of about 1400° F. or higher.

3. A method as recited in claim 2 wherein the feedstock is mixed with steam for enhancement of the cracking thereof.

4. A method as recited in claim 2 wherein said rare earth element or compound is added to said feedstock during cracking thereof.

5. A method as recited in claim 2 wherein said rare earth element or compound is added to said feedstock prior to cracking.

6. A method as recited in claim 2 wherein said rare earth element or compound is added to said feedstock in an amount of about 0.1–5000 parts of said rare earth per million parts of said feedstock.

7. A method as recited in claim 6 wherein said rare earth is added in an amount of about 5–1000 ppm per million parts of said feedstock.

8. A method as recited in claim 1 wherein said rare earth element or compound is chosen from the group consisting of rare earth elements, inorganic rare earth compounds and organic rare earth compounds.

9. A method as recited in claim 8 wherein said rare earth element or compound is elemental cerium, a cerium containing compound, elemental lanthanum, or a lanthanum containing compound.

10. A method as recited in claim 8 wherein said rare earth element or compound comprises elemental cerium or a cerium containing compound.

11. A method as recited in claim 8 wherein said rare earth element or compound comprises elemental lanthanum or a lanthanum containing compound.

12. A method as recited in claim 10 wherein said cerium containing compound is selected from the group consisting of cerous nitrate hexahydrate, cerium oxide, and ceric ammonium nitrate.

13. A method as recited in claim 11 wherein said lanthanum containing compound comprises lanthanum nitrate hexahydrate.

14. A method of inhibiting the formation and deposition of pyrolytic coke on the heated metal surfaces of the structural and associated parts of a pyrolysis furnace which is being used to crack a petroleum feedstock to produce lower and/or olefinic hydrocarbon fractions, wherein said metal surfaces are heated to a temperature of 1400° F. or higher, said method comprising adding to said feedstock a compound selected from the group consisting of cerous nitrate hexahydrate, cerium oxide, ceric ammonium nitrate and lanthanum nitrate hexahydrate, said compound being added in an amount necessary to provide from about 0.1–5,000 parts of said cerium or lanthanum in said feedstock, based upon one million parts of said feedstock.

15. A method of inhibiting the formation and deposition of pyrolytic coke on the heated metal surfaces of the structural and associated parts of a pyrolysis furnace which is being used to crack a petroleum feedstock to produce lower and/or olefinic hydrocarbon fractions, which method comprises adding to the feedstock a coke inhibiting amount of a rare earth element or rare earth containing compound, said feedstock comprising ethane, propane, butane, light naphtha, gas oils or mixtures thereof.

16. A method as recited in claim 15 wherein said feedstock comprises ethane, propane, or butane or mixtures thereof.

17. A method as recited in claim 15 wherein said rare earth element or compound is elemental cerium, a cerium containing compound, elemental lanthanum, or a lanthanum containing compound.

18. A method as recited in claim 15 wherein said rare earth element or compound comprises elemental cerium or a cerium containing compound.

19. A method as recited in claim 15 wherein said rare earth element or compound comprises elemental lanthanum or a lanthanum containing compound.

20. A method as recited in claim 18 wherein said cerium containing compound is selected from the group consisting of cerous nitrate hexahydrate, cerium oxide, and ceric ammonium nitrate.

21. A method as recited in claim 20 wherein said lanthanum containing compound comprises lanthanum nitrate hexahydrate.

* * * * *